United States Patent [19]

Gess

[11] Patent Number: 4,613,406
[45] Date of Patent: Sep. 23, 1986

[54] METHOD OF MEASURING DRAINAGE RATE

[75] Inventor: Jerome M. Gess, Bellevue, Wash.

[73] Assignee: Weyerhaeuser Company, Tacoma, Wash.

[21] Appl. No.: 699,238

[22] Filed: Feb. 8, 1985

Related U.S. Application Data

[63] Continuation of Ser. No. 481,975, Apr. 4, 1983, abandoned.

[51] Int. Cl.$^4$ .................. G01N 7/00; G01N 11/00
[52] U.S. Cl. .................................. 162/49; 73/61.4; 73/63; 162/263
[58] Field of Search ............... 162/49, 252, 258, 263, 162/254; 73/63, 61 R, 61.4

[56] References Cited

U.S. PATENT DOCUMENTS

| | | | |
|---|---|---|---|
| 2,602,325 | 7/1952 | Campbell et al. | 73/63 |
| 3,368,392 | 2/1968 | Miller | 73/63 |
| 3,688,563 | 9/1972 | Erarsson et al. | 73/63 |
| 3,838,594 | 10/1974 | Kesler | 162/263 |

FOREIGN PATENT DOCUMENTS

0926124  5/1982  U.S.S.R. .................. 162/263

OTHER PUBLICATIONS

McGill, "Measurement and Control in Paper Making", Adam Hilger Ltd., G.B., 1980, pp. 240-241.
Gess, J. M., "A New Drainage Analysis System", Mar. 1984, Tappi Journal, pp. 70-72.
Clark, James D'A., "Freeness Fallacies and Facts", vol. 53, No. 1, Jan. 1970/Tappi, pp. 108-113.

Primary Examiner—Steve Alvo

[57] ABSTRACT

The drainage quality of a pulp furnish slurry on a paper machine forming wire is predicted by the drainage tester of this invention by accounting for the effect of drainage through the paper sheet as it forms. The tester can distinguish between fast draining mechanical pulps and slower draining chemical pulps as well as predict the effects various additives will have on drainage. The apparatus includes a screen which separates furnish fibers from the slurry white water in response to a constant volume vacuum pump. Pressure differential as a function of time is recorded producing for any given furnish three distinctive points of inflection on the curve, including a first point of inflection which correlates with the wet line on a paper machine forming wire, second point of inflection which correlates with the dry line on the former and a third point of inflection which correlates with the maximum practicable removal of water from said pad by the typical former vacuum systems.

2 Claims, 5 Drawing Figures

METHOD OF MEASURING DRAINAGE RATE

This application is a continuation of application Ser. No. 481,975, filed Apr. 4, 1983, now abandoned.

BACKGROUND OF THE INVENTION

1. Field of the Invention

The invention relates to forming a paper web on a paper machine. More particularly, the invention relates to testing apparatus designed to measure drainage of water from a pulp furnish on that portion of the paper machine which forms the paper web or sheet.

2. Description of the Prior Art

In forming a pulp or paper web, a pulp furnish comprising a dilute slurry of fibers is typically flowed onto a moving wire. The wire travels across a series of foils, suction boxes and rolls which apply vacuum forces to dewater or drain away the slurry water while retaining the fibers on the wire and eventually forming the paper or pulp sheet. The formed sheet then proceeds to the paper machine pressing and drying sections for further water removal.

It is well known that paper web strength increases as the web becomes drier. The amount of water removed during forming determines the strength of the web. If drainage is slow, the machine speed may have to be reduced because the web may not be strong enough to survive the stresses which are exerted on the sheet in leaving the forming section and undergoing pressing operations. Conversely, a small improvement in the rate of drainage of water from the sheet on a wire limited machine, i.e., where wire speed is a production bottleneck, will translate into increased production. An increase in the total amount of water removal before the paper web enters the dryer section may mean increased profitability through lower drying costs. A 1% decrease in moisture content of the wet web means a 4–5% decrease in required dryer section capacity.

The driving forces for water drainage from the furnish slurry on the forming wire of the paper machine have been suggested to include: (1) hydrostatic pressure from the weight of the fiber water slurry on the wire; (2) inertial pressure from the angular impingement of the stock jet from the head box slice onto the wire; (3) hydrodynamic vacuum forces generated by motion of the wire over table rolls and drainage foils; (4) externally generated vacuum forces applied by suction boxes under the wire; and (5) pressure from rolls such as lump breaker rolls and couch presses. Drainage on a paper machine depends primarily upon vacuum forces employed during forming and the rate at which water can be removed from a particular furnish. The fiber composition of a furnish, furnish refining schedule, the total non-fiber additives package as well as the physical layout of a machine each play major roles in achieving a particular drainage level.

Improving paper web forming efficiency on a paper machine is a continual goal of all papermakers. In determining performance of a furnish on the paper machine, it is necessary to know how fast water drains from a particular furnish, and how much water can be expected to be removed by vacuum on the forming wire. Papermakers rely on drainage measurements in one form or another as a convenient rule of thumb to predict runnability of a given papermaking furnish on the former of a paper machine. Most present drainage testers such as Canadian Standard Freeness (CSF), Schopper-Riegler, Williams Precision, Drainac, etc. measure principally the rate at which water drains from a furnish before the mat is formed. Drainac is a registered trademark of Bolton-Emerson, Inc., Lawrence, Mass. The result of such tests is often called the "freeness" of a pulp furnish. The contribution of dewatering through a mat is generally ignored, however, resulting in freeness values that do not relate to performance on the paper machine. Freeness drainage testers presently available do not give a complete description of behavior of a furnish as it is formed into the paper web on the machine. Changes in furnish, refining pattern and use of chemical additives will change relationships between freeness and runnability even though the freeness value itself may not change or change in a way that is unrelated to runnability.

Increasing refining of a pulp furnish is a method of increasing the strength of the paper formed on the paper machine. The greater the refining energy imparted to a pulp, the greater is the strength potential of the web formed on the machine. However, the impact of increased refining generally is to slow the drainage rate on the wire. With chemical pulps, as degree of refining increases, there is an increase in time required for the pulp to drain and less water can be removed. However, papermakers know that furnishes containing mechanical pulps drain faster on a paper machine than do chemical pulps, even when refining levels are equal. For example, a groundwood furnish having a Canadian Standard Freeness of 150–200 ml will dewater on a fourdrinier as fast as a kraft furnish having a CSF of about 500 ml.

Freeness measures are still used, however, because no other tools are available. With experience, the papermaker has been able to set up "correction factors" that appear to work for some purposes. However, for many purposes the impact on drainage resulting from operating changes is unpredictable and present methods require on-machine trials. As an example, wet end retention aids and the like tend to decrease drainage sometimes so significantly that production must be reduced. There is, therefore, a need in industry to measure drainage in a way that responds to furnish variations, refining levels and the like and produces a result that directly relates to actual machine performance.

SUMMARY OF THE INVENTION

The apparatus and methods of use of this invention provide information beyond that provided by standard freeness testers, allowing comparison of drainage capabilities between paper furnishes. The tester gives information about drainage rates and water retention values of pulp furnishes that relate to forming and pressing on actual paper machines. The tester is capable of determining impact on drainage caused by variations in furnish pulp species, consistency, temperature, basis weight and the like. The tester can be used to determine how changes in the additives chemistry of a system such as, for example, the use of retention and drainages aids or sizes will affect the total drainage pattern of a system.

The results demonstrate that drainage time determined by the testing apparatus of this invention can differentiate between furnish species and additives while freeness testers, such as the Canadian Standard Freeness tester, cannot. There is no need to adjust drainage tester results by application of intuition or experience as is required of CSF values to permit furnish and drainage comparisons at different conditions.

The tester of this invention is capable of determining the "wet line" on a paper machine which machine tenders presently watch as a means of estimating how a furnish will ultimately dry. The wet line on the former is a visible delineation where the paper slurry appears to coalesce into a coherent sheet or web.

The tester of this invention allows measurement of single pass retention of fines or pigments or chemicals and measures their impact on drainage on the paper machine.

The ideal quantity of water that can be removed from the web by the forces available on a typical paper machine former can be measured and compared with actual values to estimate the water removal or drainage efficiency of the former machine. Drainage tester results enable papermakers to design furnishes, refining patterns and additives that maximize production from a given former system without downstream adverse drainage effects. Alternatively, given a furnish, a papermaker is now able to design an optimum former.

The testing apparatus of this invention includes a filtering means for receiving, holding and dewatering a pulp sample at substantially headbox consistency. The filter means includes a screen for separating fibers from the pulp furnish slurry and retaining a pulp mat of the furnish. The screen is designed to substantially duplicate the filtering or dewatering capability of a paper machine forming wire. A constant volume vacuum means exerts a negative pressure differential on the sample held in the filtering means. A recording means is provided for recording the pressure differential on the filter means as a function of time. The method of using the above apparatus includes introducing a sample of the slurried pulp furnish at substantially the consistency typically flowed onto an actual paper machine former into the filter means described above. The sample is subjected to a pressure differential means immediately after the sample is introduced into the apparatus which causes it to dewater. The pressure differential on the system is recorded as a function of time, including particularly a first point of inflection which correlates with air just beginning to be pulled by evacuation through the newly formed sheet on the paper machine forming wire, often called the "wet line" by papermakers; a second point of inflection which correlates with initiation of dewatering and response to vacuum forces, often called the "dry line", and; a third point of inflection which indicates water susceptible to practicable vacuum removal on a paper machine has been substantially extracted and air is being freely evacuated through the sheet. The third point of inflection may be used to evaluate the dewatering or drainage efficiency of a paper machine former. This method requires measuring the fiber content of a pad of pulp after the third point of inflection and comparing it with the fiber content of the web leaving the former section of the paper machine operation. This comparison recognizes that the third point of inflection by the test apparatus represents the ideal or maximum water that can practicably be removed from the paper web by employment of vacuum forces alone.

DESCRIPTION OF THE PREFERRED EMBODIMENTS

Figure 1:
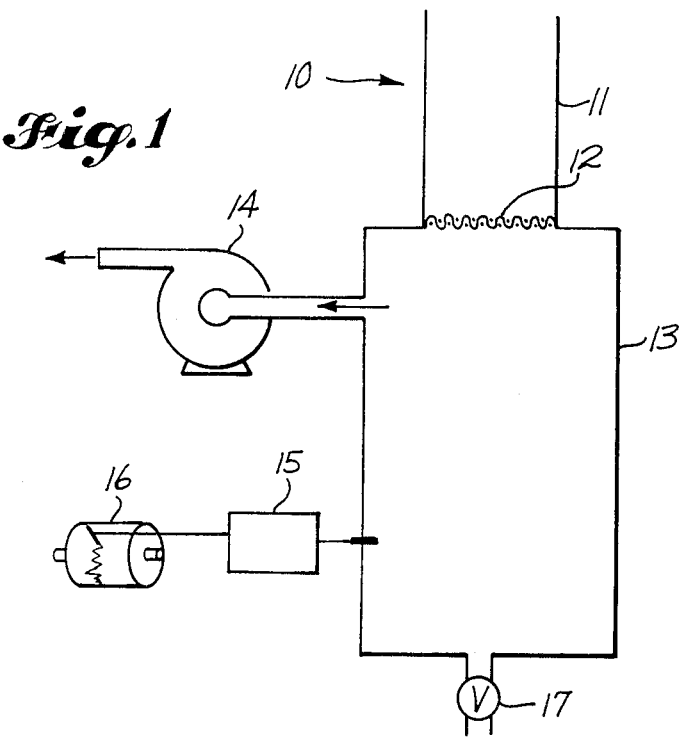
FIG. 1 is a schematic diagram of the testing apparatus of this invention.
Figure 2:
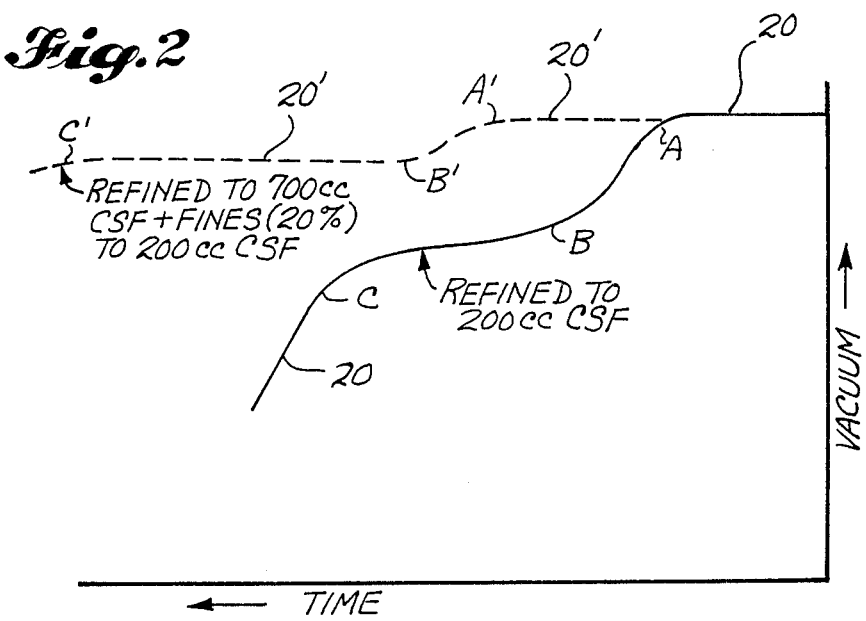
FIG. 2 shows typical recordings of pressure differential as a function of time produced by the apparatus of FIG. 1 for two pulp furnishes of identical Canadian Standard Freeness.

Referring to FIGS. 1-2, the principal features of the drainage tester of the invention are shown. A filter means 10 includes a container 11 for receiving and holding a pulp furnish slurry at a dilute consistency. consistencies similar to those typically flowing from a paper machine headbox onto the forming wire are employed. The filter means 10 includes a wire screen 12 which with respect to the slurry pulp sample retains slurry sample fibers while allowing the slurry water to pass therethrough. The screen characteristics are designed so that the screen dewatering effect substantially duplicates the dewatering capability of a paper machine forming wire. Thus, screen 12 is typically selected to have openings of about 40-100 standard mesh. Most test screens 12 are 60 or 100 mesh. The filtering means 12 is mounted on a closed receiving container 13. Seals (not shown) insure the mounting connections are vacuum tight.

A constant volume vacuum pump 14 evacuating container 13 exerts a negative pressure differential on the sample held by the filter means 10. A vacuum transducer 15 monitors the container 13 pressure differential and drives a chart recorder 16 which records pressure differential as a function of time.

A drain 17 is provided to permit sampling of the filtrate or "white water" for retention studies and the like.

The combination of sample size, screen diameter and vacuum pump capacity are balanced to produce reasonable testing times. The filter screen 12 is typically 20-70 mm in diameter, depending upon vacuum pump 14 capacity. For most furnishes about a 50 mesh screen for a vacuum pump of 35 L/min. has proven convenient.

In operation, a pulp furnish slurry sample of 100-200 ml, mildly agitated by inverting its container a number of times, is poured into the filtering means receiving container 11. For exceptionally slow draining furnishes such as newsprint, for example, a 20 ml sample and the smaller, 25 mm diameter, screen would be used for the same capacity vacuum pump. The pulp slurry consistency selected may range from about 0.15 to 1.5% fiber content by weight, depending upon the consistency used on the paper machine forming system of interest. In general, a 0.8% consistency is used as a standard consistency, as a matter of convenience. The vacuum pump and recorder are simultaneously initiated immediately after the pulp slurry is poured into the receiving container.

Referring to FIG. 2, the solid line trace 20 of pressure differential or vacuum as a function of time produced by the recorder is shown and is typical of all pulp furnishes. At the start of the drainage process, the liquid pulp slurry sample seals the system and there is a rapid rise in vacuum to a maximum level. The free water not bound to the fibers begins draining through the screen. Free water is that water in the system that is primarily affected by other water molecules in the system and is substantially unaffected by solids in the system. A mat of pulp forms from the dilute slurry on screen 12 under the vacuum developed by the constant volume air flow pump 14. The water draining from the pad is water held on the surfaces of the pulp fibrils, principally by surface tension forces. The water above the screen exerts a pressure on the mat and causes some compacting of the pulp layer. Most of the compressing of the mat occurs as the water level recedes from the top of the mat with the water surface tension forces exerting a downward pulling force on the pad.

As the drainage test proceeds, the FIG. 2 plot of drainage time versus vacuum shows three distinctive points of inflection, labeled A, B and C.

The high initial vacuum continues to a point of inflection A where there is a significant drop in vacuum. The "A break" represents formation of the pad and drainage through it, including some compression of the web by water surface tension forces, until air begins to be pulled through the pad. The first phase of drainage ends when the fibers have formed into a web which roughly correlates with the appearance of the wet line on the paper machine.

From A to B on the FIG. 2 plot, further free water is removed. This second phase of the drainage process includes compaction or compression of the web by vacuum forces. Essentially, water is removed by the decrease in the void volume of the web under the influence of vacuum forces. This portion of the drainage process ends with the appearance of the second point of inflection, point B on the FIG. 2 plot, which appears to correlate with the appearance of the dry line on the paper machine. In this zone on the paper machine, water removal is accomplished primarily by vacuum, typically flat vacuum boxes or similar devices employing, in general, forces stronger than the earlier mild forming forces such as gravity and forming table foil vacuum forces.

In the B-C phase of drainage, the remaining free water is removed. Air flows through the mat pulling out still more water and further compressing the mat. After a certain point, the mat will no longer compress and air is pulled substantially freely through the mat. At this point, the web can no longer be dewatered by vacuum forces alone and typically enters the pressing section of the paper machine. This point is marked on the FIG. 2 plot as the third point of inflection, point C.

The amount of water removed in the B-C zone can be used to estimate pump capacities, and storage in that zone. The longer the B-C zone in time, the greater the amount of vacuum required to completely drain the furnish.

Point C is correlatable with the ideal condition of the web at the couch of the paper machine, i.e., just before departure from the forming section into pressing. By determining the percent solids of the system at point C a theoretical maximum obtainable solids value is calculable which, when compared with actual machine values, constitutes a measure of wire of former efficiency.

The turbidity of the drainage waters from instrument is a measure of the expected retention of fines, pigments or chemicals on the paper machine.

The time recorded to reach a first point of inflection A is most pronounced and is sensitive to furnish species and wood pulp manufacturing processes, compositions, degree of refining, chemical additives and fines content of the furnish. The first phase of drainage is also limited by characteristics or condition of the water present, such as viscosity or height of water with the respect to the forming wire and so on. The appearance of point A is a unique characteristic of each pulp furnish. The time, in seconds, required to reach point A from the establishment of constant vacuum is called the "Drainage Number" of a pulp furnish. As noted above, Drainage Number is a function of stock consistency. As a matter of convenience a Standard Drainage Number is defined as the time required to reach the A break of a 100 ml sample of a 0.8% by weight pulp fiber furnish slurry sample. Such standardization permits direct comparison between the various furnishes.

Figure 3:
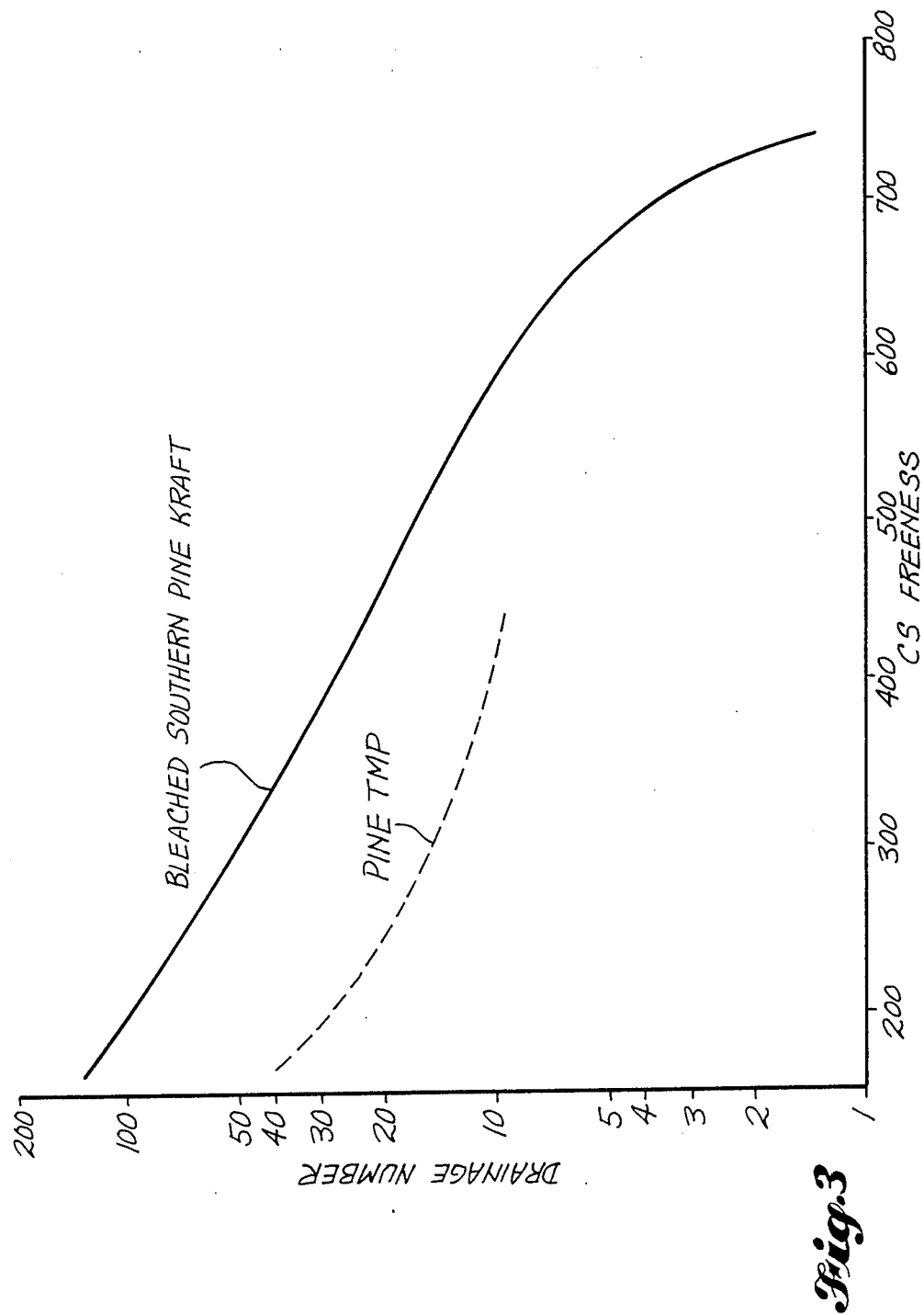
FIG. 3 shows the capability of the apparatus and method of the invention to distinguish between mechanical and chemical pulps of equal CSF.

The drainage tester of this invention can distinguish between fast draining mechanical pulps and slower draining chemical pulps which many drainage testers such as CSF cannot. The relationship between CSF and the Standard Drainage Number of this invention is semilogarithmic, as suggested by FIG. 3. FIG. 3 shows, as long empirically known by paper-makers, that mechanical pulp, as represented by a pine thermomechanical pulp furnish, is much faster draining than chemical pulp, for example a bleached southern pine kraft, even though both have identical CSF.

The nature of refining and the nature of the drainage test suggest the reasonableness of the results which are achieved by the tester of this invention. As a layer of fibers is deposited on the forming screen, the water draining from the slurry must flow through pores and channels between the fibers. The fiber mat as it builds forms an increasingly long and tortuous path through which remaining water may pass, creating an ever-increasing resistance to subsequent flow. Compression of the mat by slurry weight or head and surface tension as water drains away further reduces the cross-sectional area through which water must drain. The greater the flow resistance, the longer it will take for a pulp slurry to drain. Refining a pulp increases the swelling and fibrillation of fibers reducing the overall cross sectional area of the pores and channels that are created during mat formation, increasing resistance to flow beyond that of lesser refined pulps. Refining increases the surface area of the individual fibers. The fibers hold more water and that water is more tightly bound to the fibers, further reducing the open area of the pulp mat and ease with which drainage proceeds. As expected and shown in FIG. 3, Drainage Number increases as level of refining of the pulp increases (as indicated by decreasing CSF).

It is well known that the presence of short fibers or fines in a furnish will slow the drainage of the stock on the former. The excessive presence of fines will as a practicality require a reduction in refining to accommodate the slower drainage. As a consequence of reducing refining, sheet strength is reduced, for example. The effect on drainage of the fines present in the furnish can be determined by use of the present invention.

As an example, a pulp furnish was refined to 200 CSF. A second sample of the identical pulp was refined to 700 CSF. A fines portion of the same species pulp was added to the second sample to reduce the CSF value to 200 CSF. FIG. 2 shows a plot 20' of drainage time for the fines containing sample and plot 20 for the unmodified sample. FIG. 2 shows that the Drainage Number A' of the fines modified sample is greater than that of the first sample, even though the CSF values are identical. The present tester produces results consistent with manufacturing experience, thus emphasizing that results of the tester of this invention for different furnishes may be directly compared in contrast to such tests as CSF.

An important feature of the invention is that the effluent white water or filtrate from the test apparatus of this invention can be collected and the solids contents thereof measured. It has been found that the quality of this effluent is such that analysis can provide an estimate of how an additive, for example, will perform on an actual paper machine. The following example and FIGS. 4-5 demonstrate this capability.

EXAMPLE

It was desired to compare the impact on drainage of two additives designed to improve retention of fiber fines. Improved retention of fines prevents their buildup in white water and hence subsequent adverse impact on drainage when white water is used to dilute machine chest pulp. The test was performed using a newsprint pulp furnish, formed on a Bel Baie II twin wire former. It is required in this particular process that the wet line of stock be as close to the couch as possible for maximum sheet formation production. The arrangement was such that any loss in immediate drainage, even though it might over time improve drainage, would in the short run cause the machine to slow and lose critical production. The additives to be compared were Accurac 135, a cationic polyacrylamide, manufactured by American Cyanamid of Stamford, Conn. and CP-13, a cationic guar gum manufactured by Celanese Corporation of Louisville, Ky. Accurac and CP-13 are registered trademarks of their respective manufacturers.

The drainage tester in this test included a 300 ml glass funnel mounted on a glass vacuum flask base. A 100 mesh, 47 mm diameter stainless steel screen and fluorcarbon gaskets are held between the funnel and the base flask with a spring clamp. This combination of screen, gaskets and a stopper for mounting on the base flask is a Millipore Filter Unit, Catalog Number XX1004730, manufactured by Millipore Corporation of Bedford, Mass. Millipore is a registered trademark of Millipore Corporation. At the bottom of the flask is a stop cock and rubber tubing for discharge of drainage or white water after each test. The base flask is connected by means of tubing to a second flask, which serves a water trap. Mounted at the top of the second flask is a pressure transducer which is connected to a variable speed Soltec recorder, model No. S-4201 (Soltec Coporation, Sun Valley, Calf.). A VWR Scientific rotary vacuum pump runs at a constant speed of 36 liters per minute of air, evacuating the system and imparting the necessary test vacuum on the filter unit.

Figure 4:
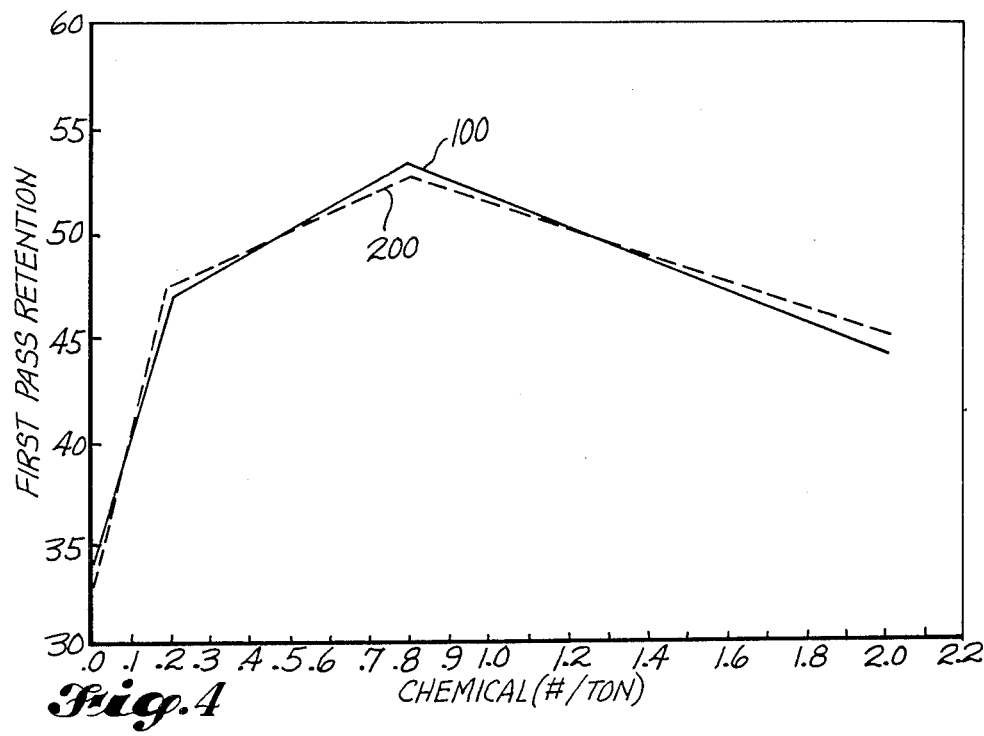
FIG. 4 shows percentage retention versus chemical addition rates for two retention aids.
Figure 5:
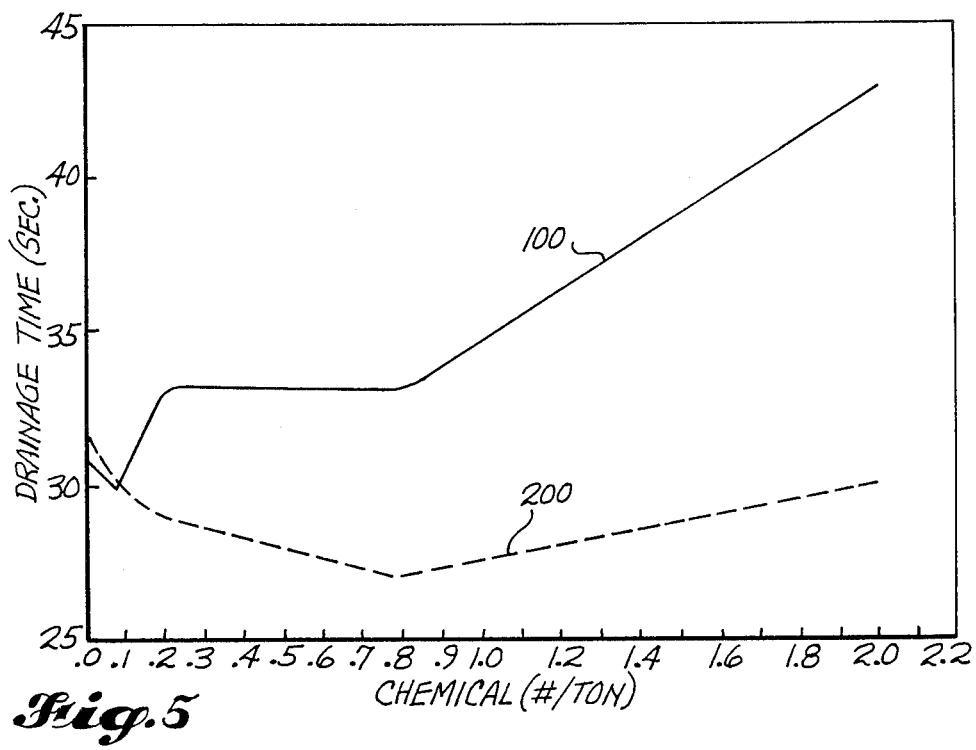
FIG. 5 shows impact on drainage of the additives of FIG. 4.

The pulp furnish sample was diluted with tap water to about headbox consistency of roughly 0.4% solids at 24±3° C. The 0.4% slurry is measured out and diluted further if necessary to produce the 200 ml sample, depending upon desired test consistency. Each 200 ml of dilute slurry is placed in a graduated cylinder. The stainless steel screen is scrubbed under tap water and installed in place drained but wet. The slurry is gently mixed by inverting the cylinder a number of times. The pulp is then poured into the glass funnel over a period of about three seconds, after which the vacuum pump is turned on. The tests were run for the range of additions levels proposed for mill use of 0.3-1.5 lbs/ton for CP-13 and 0.5-2.0 lbs/ton for Accurac 135. The white water from the tests was collected and percentage first pass retention was measured. As shown in FIG. 4, retention as a function of the amount of chemical added per ton was plotted. Accurac 135, curve 100, and CP-13, curve 200, retained fines to about the same degree. However, a plot of Drainage Number (that is the time to the "A break" point of inflection) as a function of chemical addition rate as shown in FIG. 5 demonstrates that the Accurac 135 significantly slowed drainage while CP-13 had virtually no impact on drainage rate or time.

A mill trial of both additives was made on the Bel Baie II former. Bell Baie II is a registered trademark of Beloit Corporation, Beloit, Wis. The Accurac 135 trial had to be halted after six hours because the drainage slowdown required a decrease in paper machine speed of 3700 ft/min to 3450 ft/min. The CP-13 trial was successful and caused no drainage-related problems on the former.

The tester affords a method of determining whether a machine is wire limited with respect to production rate. The percentage fiber content of the wet pad formed on the screen of the tester apparatus is, immediately after the C break, removed from the screen and weighed. The pulp pad is pressed between two blotters, dried at 105° C. to a constant weight and then weighed to the nearest 0.001 g. The pad percent solids is calculated as dry weight divided by wet weight times 100. A sample of the paper web just as the web leaves the forming section of the paper machine is collected and percent solids determined as described above. The percentage fiber content of the pad is related to the maximum amount of water that can be removed by practicable wires, foils and vacuum means in the forming section of the paper machine. Thus, the ratio of the test sample, fiber content to the paper machine sample fiber content is related to the efficiency of the paper machine. If a ratio is in the range of 90%, then the wire is efficient and probably not limiting production.

I claim:

1. In a method of measuring drainage rate of a pulp furnish for making paper products to predict how said furnish will dewater on a paper machine forming wire, the method being of the type wherein a slurry sample of the furnish is placed in a holding container having a screen bottom for separating furnish solids from slurry water, the slurry then being dewatered so as to form a wet pad of furnish solids on the screen with the water draining therethrough, the improvement comprising:

placing a finite sample of slurry in the holding container;

dewatering the slurry sample while subjecting it to a pressure differential created by providing a reduced pressure beneath the holding container screen while the upper surface of the slurry is exposed to the atmosphere;

recording, simultaneously with beginning dewatering the sample, the pressure differential across the sample as a function of time throughout the entire period when water is being removed, particularly recording a first point of inflection where pressure differential decreases as air first begins to be drawn through the pad on the screen, a second point of inflection marking the point at which pad compression in response to the pressure differential effectively ends, and a third point of inflection marking the point where water is no longer being removed but air continues to be drawn through the pad; and relating said recorded points of inflection to drainage characteristics of a pulp furnish on a paper machine forming wire.

2. The method of claim 1 in which the slurry being tested has a consistency essentially the same as that used in papermaking at the location where the stock flows from the headbox onto the forming wire.

* * * * *